US008747308B2

(12) United States Patent
Muzzammel

(10) Patent No.: US 8,747,308 B2
(45) Date of Patent: Jun. 10, 2014

(54) LATERAL VAGINAL RETRACTOR

(76) Inventors: Mohiuddin M. Muzzammel, Reston, VA (US); Rashida Muzzammel, legal representative, Reston, VA (US)

(\*) Notice: Subject to any disclaimer, the term of this patent is extended or adjusted under 35 U.S.C. 154(b) by 8 days.

(21) Appl. No.: 13/507,665

(22) Filed: Jul. 19, 2012

(65) Prior Publication Data
US 2012/0316399 A1  Dec. 13, 2012

Related U.S. Application Data

(63) Continuation of application No. 12/583,376, filed on Aug. 20, 2009, now abandoned.

(60) Provisional application No. 61/190,448, filed on Aug. 29, 2008.

(51) Int. Cl.
*A61B 1/32* (2006.01)

(52) U.S. Cl.
USPC .......................................................... 600/220

(58) Field of Classification Search
USPC ......... 606/184, 185, 190, 193, 196, 197, 214, 606/215, 218–224; 433/93, 157, 162
See application file for complete search history.

(56) References Cited

U.S. PATENT DOCUMENTS

| 52,014 | A | | 1/1866 | Bartlett |
| 90,319 | A | * | 5/1869 | Somers ........................ 294/99.2 |
| 1,474,497 | A | * | 11/1923 | Stolper ......................... 600/240 |
| 2,575,253 | A | | 11/1951 | Bicek |
| 3,651,800 | A | | 3/1972 | Wilbanks |
| 3,729,006 | A | | 4/1973 | Wilder et al. |
| 5,377,667 | A | | 1/1995 | Patton et al. |
| 5,499,964 | A | | 3/1996 | Beck et al. |
| 6,471,515 | B2 | | 10/2002 | Feuer |

\* cited by examiner

*Primary Examiner* — Anu Ramana
(74) *Attorney, Agent, or Firm* — Joseph H. McGlynn

(57) ABSTRACT

An attachment which can be used with a vaginal speculum. The attachment can be used with a vaginal speculum. The attachment has a pair of arms on one end which will engage the fornix lateral to the cervix of a women's vagina, and a U-shaped curved portion on the other end which will allow a doctor to engage the attachment with a vaginal speculum in order to spread a patient's lateral, as well as vertical, walls at the same time.

10 Claims, 4 Drawing Sheets

LATERAL VAGINAL RETRACTOR

Applicant claims priority of Provisional Ser. No. 61/190,448, filed Aug. 29, 2008. The present application is a Continuation of patent application Ser. No. 12/583,376, filed Aug. 20, 2009, now pending.

BACKGROUND OF THE INVENTION

This invention relates, in general, to specula, and, in particular, to a lateral vaginal specula.

DESCRIPTION OF THE PRIOR ART

In the prior art various types of speculum have been proposed. For example, U.S. Pat. No. 2,575,253 to Bicek discloses a vaginal speculum which has a curved portion on one end and a handle with a hook on the other end providing a means for the user to manipulate the speculum.

U.S. Pat. No. 3,651,800 to Wilbanks discloses a jaw deflector which has a curved portion on one end and a handle with a hook on the other end providing a means for the user to manipulate the deflector.

U.S. Pat. No. 3,729,006 to Wilder et al discloses surgical retractors with a hook portion on one end and a series of serrations on the other end to provide hand holds for the surgeon, allowing the surgeon to manipulate the retractors.

U.S. Pat. No. 5,499,964 to Beck et al discloses a vaginal speculum with two portions that can be separated and held apart by a screw member.

SUMMARY OF THE INVENTION

The present invention is directed to an attachment which can be used with a vaginal speculum similar to the speculum disclosed by Beck et al. The attachment has a pair of arms on one end which will engage the interior of a women's vagina, and a U-shaped curved portion on the other end which will allow a doctor to engage the attachment with a vaginal speculum in order to spread a patient's lateral, as well as vertical, walls at the same time.

It is an object of the present invention to provide an attachment which can be used with a vaginal speculum to engage and spread a patient's lateral and vertical walls at the same time.

It is an object of the present invention to provide an attachment which can be used with any vaginal speculum.

These and other objects and advantages of the present invention will be fully apparent from the following description, when taken in connection with the annexed drawings.

DESCRIPTION OF THE PREFERRED EMBODIMENT

Figure 2:
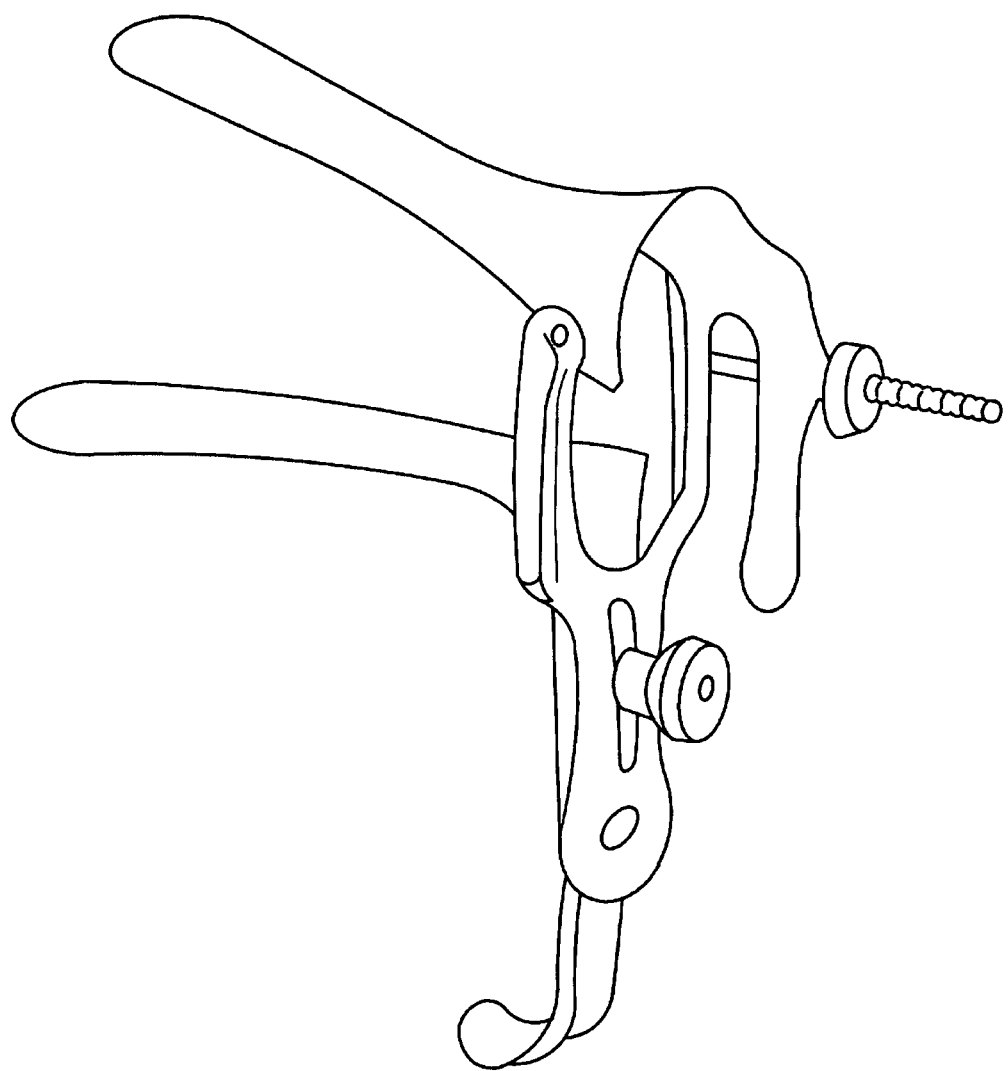
FIG. 2 is a view of a prior art speculum.
Figure 3:
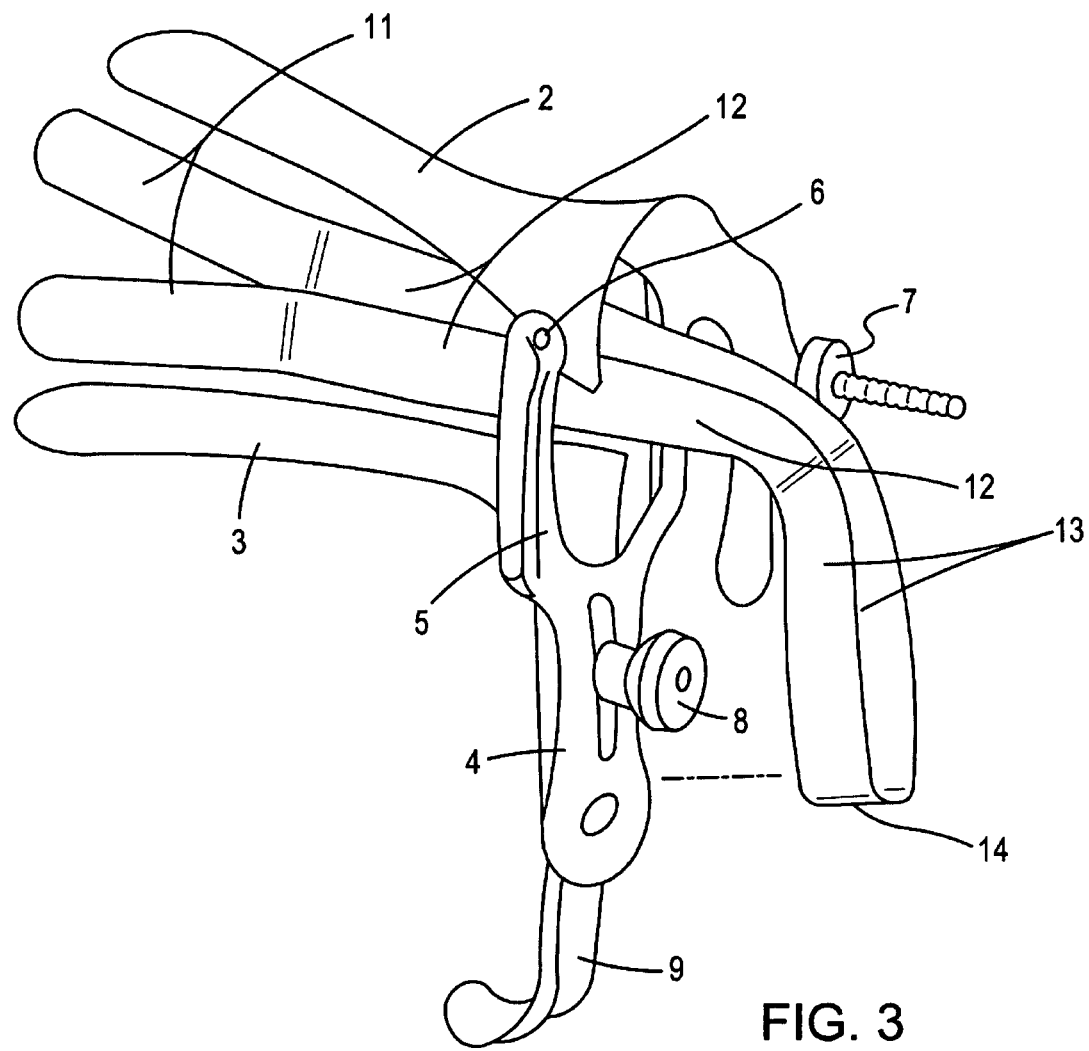
FIG. 3 is a view of the present invention used with a prior art speculum.

Referring now to the drawings in greater detail, FIG. 2 shows a typical prior art speculum 1 which is used by doctors in various gynecological procedures such as examinations, hysterectomies and surgical treatments of cancer and other diseases. During these types of treatments, a vaginal speculum is typically employed to dilate the vaginal cavity so that the uterus or cervix may be operated upon in an unobstructed manner. As shown in FIG. 3, the speculum has an upper blade 2 and a lower blade 3 which engage the inner walls of the upper and lower portions of the vagina in order to dilate the vagina in a vertical direction.

The lower blade 3 is attached to a body 4 which has a pair of arms 5 extending vertically therefrom. The upper blade 2 is pivotally attached at 6 to the upper portion of the arms 5. Adjustment means 7 is used to spread the upper and lower blades 2, 3 and latch knob 8 is used to lock the blades in a selected position. Handle portion 9 is used by the doctor to manipulate the instrument. Since the speculum 1 is a conventional instrument well known in the prior art, no further description is necessary.

While the prior art speculum 1 works in its intended manner, i.e. dilating the vagina in a vertical direction, it has no function that will assist the doctor in dilating the vagina in a horizontal direction. In the past, two specula 1 have been used with one positioned at a right angle to the other. This has many drawbacks because the body 4, arms 5, handle 9, and the adjusting and locking means 8 tend to obstruct the doctor's view and otherwise interfere with the particular surgical procedure being attempted.

Figure 1:
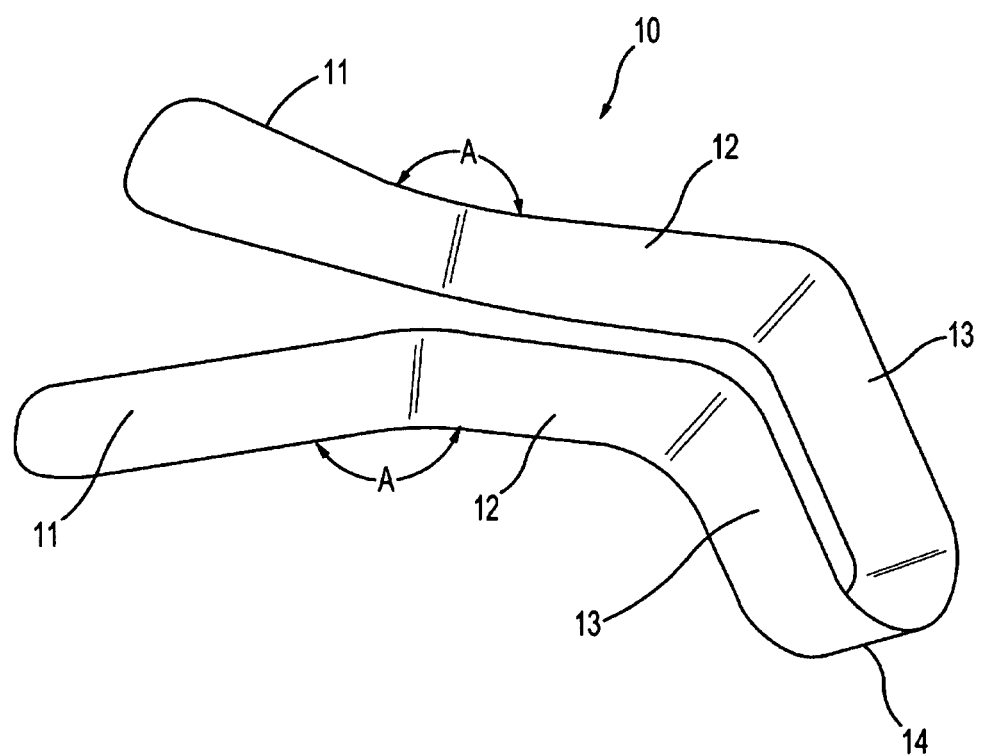
FIG. 1 is a perspective view of the present invention.
Figure 4:
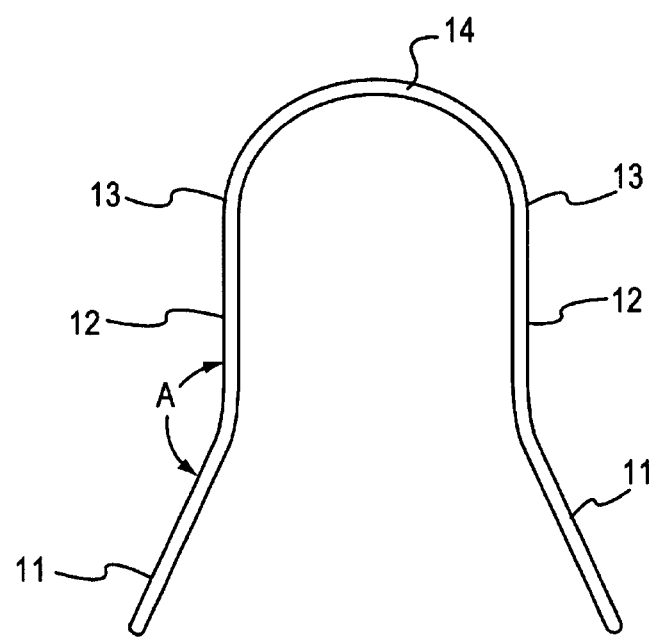
FIG. 4 is a top view of the present invention.

The attachment of the present invention 10, shown in FIGS. 1, 3 and 4, solves the problems associated with using two specula, as described above. The present invention 10 is an attachment which is designed to be used with the prior art speculum 1, and comprises a blade having a first end with a pair of arms 11. The arms 11 have a free end portion. The arms 11 each comprise a first portion that extends in the same direction away from their respected free ends to form a trough therebetween. The area of arm 11 closest to the adjacent arm 11 is the inner surface of each of the arms 11. The surface of arm 11 furthest from the adjacent arm 11 is the outer surface of each of the arms 11. A second portion 12 of each arm 11 is joined to the first portion and extends away from the first portion toward the second end of the attachment.

The second end of the attachment has a handle portion composed of a pair of arms 13 which are joined by a curved portion 14 to each other. The arms 13 are also joined to the second portion of the arms 11 thereby forming a substantially L-shape. The second portion of the arms 11 extend in a first plane and the arms 13 extend from the second portion of the arms 11 in a second plane. The arms 13 and the curved portion 14 can be used by the doctor as a handle to manipulate or otherwise position the attachment 10.

The attachment 10 can be made from any type of material such as, but not limited to, plastic or metal. In addition the attachment can be made in different sizes, such as small, medium or large, for accommodating patients of different sizes or for different types of surgical procedures. The attachment can be used in a variety of procedures such as, but not limited to, pap smears, cryotherapy or leep procedures, colposcopy, or cervical laser procedures.

FIG. 3 shows the attachment of the present invention in use with the speculum of the prior art. The speculum has been inserted into the vagina and has been adjusted properly to dilate the vagina in a vertical direction. Since the doctor needs to dilate the vaginal in a horizontal direction, as well, the attachments 10 of the present invention have been secured to the arms 5 of the speculum. This is accomplished by engaging the outer sides of the arms 12 which form a second portion, with the inner sides of the arms 5. The terminal or first end of the blade portion 10 will be positioned by placing the arms 11 on the lateral vaginal fornix lateral to the cervix for better exposure of the cervix. Once engaged with the inner side walls of the vagina, this will allow the doctor to dilate the vagina in a horizontal direction by manipulating, by hand or with instruments, the portions 11, 12 or the handle 13, 14. Since the attachment is not as bulky or cumbersome as the speculum, and the handle is connected at an elevation below the second portion 12 the doctor's vision will not be as obstructed, and he/she will have greater freedom to manipulate instruments within the vaginal cavity.

Also, it should be noted that as shown in FIGS. 1 and 4, an angle A exists between the outer surface of arm portions 12 and outer surface of the portions 11. This angle is preferably slightly less than 180°. This will create an angle between the inner surface of arm portions 12 and inner surface of the portions 11 of more than 180°. The angle of the arms will allow a wide exposure of the cervix to allow the physician to work as unimpeded as possible. In addition, the angle will make it harder for the present invention to become accidentally dislodged from the speculum.

In addition, although the present invention has been describe for use with a vaginal speculum, it should be noted that it could also be used with any type of retractor in any type of surgical procedure where the doctor has to spread a cavity in a vertical as well as a horizontal direction in order to perform a procedure.

Although the Lateral Vaginal Retractor and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

I claim:

1. A lateral vaginal retractor in combination with a speculum for use in a variety of gynecological procedures, said speculum comprising:
    an upper blade and a lower blade for engaging inner walls of upper and lower portions of a vagina in order to dilate the vagina in a vertical direction,
    said lower blade is attached to a body which has a pair of arms extending vertically therefrom, and
    said upper blade is pivotally attached to an upper portion of said arms extending vertically from said lower blade,
    adjustment means for spreading said upper and lower blades, and means for locking the upper and lower blades in a selected position, and
    said lateral vaginal retractor comprising:
    a first end and a second end,
    a pair of arms extending from said first end toward said second end,
    each of said pair of arms comprising a first portion and a second portion,
    each said first portion having a free end portion remote from said second portion,
    each said first portion diverging from another said first portion thereby creating an angle between said first portions, and
    each said first portion creating an angle with each said second portion, and
    a handle portion, and
    wherein said handle portion comprises a first handle portion and a second handle portion, and
    each said second portion extending from said first handle portion and said second handle portion, respectively, and
    an arm portion joined to each said second portion, and
    wherein each said second portion extends from each said first portion in a first plane, and
    wherein said first plane contains a lower surface of a second portion of each arm, and
    wherein each handle portion extends from each said second portion in a second plane, such that each handle portion forms a substantially L-shape with each said second portion, and
    wherein said second plane contains upper edges of the first and second handle portions and extends downwardly with respect to said first plane, and
    wherein the pair of arms and the handle portion form a single continuous strip extending between the free end portions.

2. The lateral vaginal retractor in combination with a speculum as claimed in claim 1 wherein said first portions have an inner surface and an outer surface, and
    said second portions have an inner surface and an outer surface, and
    said angle between each said first portion and each said second portion is measured between said outer surface of said first and second portions.

3. The lateral vaginal retractor in combination with a speculum as claimed in claim 2 wherein an angle measured between an inner surface of each said first portion and an inner surface of each said second portion is more than 180 degrees.

4. The lateral vaginal retractor in combination with a speculum as claimed in claim 2 wherein said angle between each said first portion and each said second portion is less than 180 degrees.

5. The lateral vaginal retractor in combination with a speculum as claimed in claim 1 wherein said handle portion comprises an arm portion connected to each said second portion.

6. The lateral vaginal retractor in combination with a speculum as claimed in claim 5 wherein said handle portion further comprises a curved portion connected to each said second portion.

7. The lateral vaginal retractor in combination with a speculum as claimed in claim 5 wherein said handle portion is joined to said second portion and said handle portion extends to an elevation below said second portion.

8. The lateral vaginal retractor in combination with a speculum as claimed in claim 1 wherein said first portions have an inner surface and an outer surface, and
    said second portions have an inner surface and an outer surface, and
    said outer surfaces of said second portions engage inner portions of said pair of arms extending vertically from said body.

9. The lateral vaginal retractor in combination with a speculum as claimed in claim 1 wherein said second portions extend between said upper and lower blades.

10. A lateral vaginal retractor for use with a speculum in a variety of gynecological procedures, said lateral vaginal retractor comprising:
    a first end and a second end,
    a pair of arms extending from said first end toward said second end,
    each of said pair of arms comprising a first portion and a second portion,
    each said first portion having a free end portion remote from said second portion,
    each said first portion diverging from another said first portion thereby creating an angle between said first portions, and each said first portion creating an angle with each said second portion, and a handle portion, and wherein said handle portion comprises a first handle portion and a second handle portion, and each said second portion extending from said first handle portion and said second handle portion, respectively, and an arm portion joined to each said second portion, and wherein each said second portion extends from each said first portion in a first plane, and wherein said first plane contains a lower surface of a second portion of each arm, and wherein each handle portion extends from each said second portion in a second plane, such that each handle portion forms a substantially L-shape with each said second portion, and wherein said second plane containing upper edges of the first and second handle portions extends downwardly with respect to said first plane, and wherein the pair of arms and the handle portion form a single continuous strip extending between the free end portions.

* * * * *